US012291705B2

(12) United States Patent
Kirchhoff et al.

(10) Patent No.: US 12,291,705 B2
(45) Date of Patent: May 6, 2025

(54) METHOD FOR STIMULATING THE GROWTH OF A BIOMASS, CONTAINED IN A LIQUID, INSIDE A BIOREACTOR

(71) Applicant: Fraunhofer-Gesellschaft zur Förderung der angewandten Forschung e.V., Munich (DE)

(72) Inventors: Volker Kirchhoff, Dresden (DE); André Weidauer, Dresden (DE); Jessy Schönfelder, Dresden (DE); Gaby Gotzmann, Dresden (DE); Christiane Wetzel, Dresden (DE); Jörg Kubusch, Dresden (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 1070 days.

(21) Appl. No.: 17/282,513

(22) PCT Filed: Sep. 25, 2019

(86) PCT No.: PCT/EP2019/075929
§ 371 (c)(1),
(2) Date: Apr. 2, 2021

(87) PCT Pub. No.: WO2020/069944
PCT Pub. Date: Apr. 9, 2020

(65) Prior Publication Data
US 2021/0380964 A1    Dec. 9, 2021

(30) Foreign Application Priority Data
Oct. 5, 2018 (DE) ............ 10 2018 124 666.8

(51) Int. Cl.
C12N 13/00 (2006.01)
C12M 1/00 (2006.01)
C12M 1/06 (2006.01)
C12M 1/42 (2006.01)

(52) U.S. Cl.
CPC ............ *C12N 13/00* (2013.01); *C12M 21/02* (2013.01); *C12M 23/22* (2013.01); *C12M 27/02* (2013.01); *C12M 29/18* (2013.01); *C12M 29/26* (2013.01); *C12M 35/02* (2013.01)

(58) Field of Classification Search
CPC . C12N 13/00; C12N 1/00; C12N 1/12; C12N 1/14; C12N 1/20; C12M 21/02; C12M 23/22; C12M 27/02; C12M 29/18; C12M 29/26; C12M 35/02
See application file for complete search history.

(56) References Cited

U.S. PATENT DOCUMENTS

| | | | |
|---|---|---|---|
| 3,988,588 A | 10/1976 | Offermann | |
| 2003/0138346 A1 | 7/2003 | Gunn et al. | |
| 2007/0170121 A1 | 7/2007 | Mukaddam et al. | |
| 2009/0011492 A1* | 1/2009 | Berzin | C12M 23/08 435/257.1 |
| 2009/0035835 A1 | 2/2009 | Slavin | |
| 2010/0035337 A1 | 2/2010 | Bahnemann et al. | |
| 2010/0124583 A1* | 5/2010 | Medoff | C12P 13/14 536/56 |
| 2013/0039810 A1 | 2/2013 | Riechers | |
| 2016/0158339 A1* | 6/2016 | Ulbert | A61K 41/10 424/206.1 |
| 2016/0289625 A1 | 10/2016 | Cizek et al. | |
| 2021/0379218 A1* | 12/2021 | Kirchhoff | A61L 11/00 |

FOREIGN PATENT DOCUMENTS

| | | |
|---|---|---|
| CN | 101065154 A | 10/2007 |
| CN | 102910701 A | 2/2013 |
| CN | 106029215 A | 10/2016 |
| CN | 107624128 A | 1/2018 |
| DE | 20 2009 010 255 U1 | 11/2009 |
| DE | 10 2009 057 698 A1 | 6/2011 |
| DE | 10 2010 007 559 A1 | 8/2011 |
| EP | 2 135 624 A1 | 12/2009 |
| JP | 2000316383 A * | 11/2000 |
| WO | WO 01/23007 A1 | 4/2001 |
| WO | WO 2008/055552 A1 | 5/2008 |

(Continued)

OTHER PUBLICATIONS

Machine generated translation of JP-2000316383-A. Espacenet. Original document published Nov. 21, 2000. Translation generated Apr. 1, 2024. (Year: 2000).*

(Continued)

*Primary Examiner* — Aaron J Kosar
*Assistant Examiner* — Andrew T Moehlman
(74) *Attorney, Agent, or Firm* — Crowell & Moring LLP

(57) ABSTRACT

A method may be provided for stimulating the growth of a biomass, which is mixed with a liquid inside a bioreactor, by means of ionising radiation. The following method steps are used: a) exposing a first partial volume of the liquid in the bioreactor to ionising radiation, the first partial volume comprising at most 10% of the liquid volume in the bioreactor; b) mixing the first partial liquid volume, which has been exposed to ionising radiation, with the second partial liquid volume, which has not been exposed to ionising radiation, in the bioreactor; c) repeating method steps a) and b) multiple times, each partial volume of the liquid in the bioreactor being exposed to a total radiation dose of at most 50 Gy on statistical average.

12 Claims, 2 Drawing Sheets

(56) References Cited

FOREIGN PATENT DOCUMENTS

| WO | WO 2011/116969 A1 | 9/2011 |
|----|-------------------|--------|
| WO | WO 2015/047298 A1 | 4/2015 |
| WO | WO 2017/056695 A1 | 4/2017 |
| WO | WO 2017/211990 A1 | 12/2017 |

OTHER PUBLICATIONS

Jeong et al. "Effect of continuous exposure to low-dose-rate gamma irradiation on cell growth and lipid accumulation of marine microalgae." Aquaculture International 25 (2016): 589-601 (Year: 2016).*

Tale et al., "Effect of gamma irradiation on lipid accumulation and expression of regulatory genes involved in lipid biosynthesis in *Chlorella* sp.", J Appl Phycol, (2018), 30:277-286 (Year: 2017).*

International Search Report for Patent Application No. PCT/EP2019/075929, dated Jan. 16, 2020, pp. 1-6.

Abomohra, A. et al., "Effect of Gamma Radiation on Growth and Metabolic Activities of Arthrospira Platensis", *Braz, Arch, Biol. Technol.*, vol. 59 No. 16150476, Jan./Dec. 2016, pp. 1-11.

Jeong, Dong Hyeok, et al., "Effect of continuous exposure to low-dose-rate gamma irradiation on cell growth and lipid accumulation of marine microalgae",*Aquaculture International*, Springer, Netherlands, vol. 25, No. 2, Aug. 26, 2016, pp. 589-601.

Stebbing, A.R.D., "Hormesis-stimulation of colony growth in Campanularia flexuosa (hydrozoa) by copper, cadmium and other toxicants", *Aquatic Toxicology, Elsevier*, Amsterdam, Netherlands, vol. 1, No. 3-4, Nov. 30, 1981, pp. 227-238.

Jeong, Dong Hyeok, et al., "Effect of continuous exposure to low-dose-rate gamma irradiation on cell growth and lipid accumulation of marine microalgae",*Aquaculture International*, Springer, Netherlands, vol. 25, No. 2, Aug. 26, 2016, pp. 589-601 (13 pp.).

Office Action dated Sep. 3, 2024 for Korean Patent Application No. 10-2021-7013578, including English translation (17 pp.).

* cited by examiner

METHOD FOR STIMULATING THE GROWTH OF A BIOMASS, CONTAINED IN A LIQUID, INSIDE A BIOREACTOR

CROSS-REFERENCE TO RELATED APPLICATIONS

This application is a 371 nationalization of international patent application PCT/EP2019/075929 filed Sep. 25, 2019, which claims priority under 35 USC § 119 to German patent application 102018124666.8 filed Oct. 5, 2018. The entire contents of each of the above-identified applications are hereby incorporated by reference.

DETAILED DESCRIPTION

Figure 1:
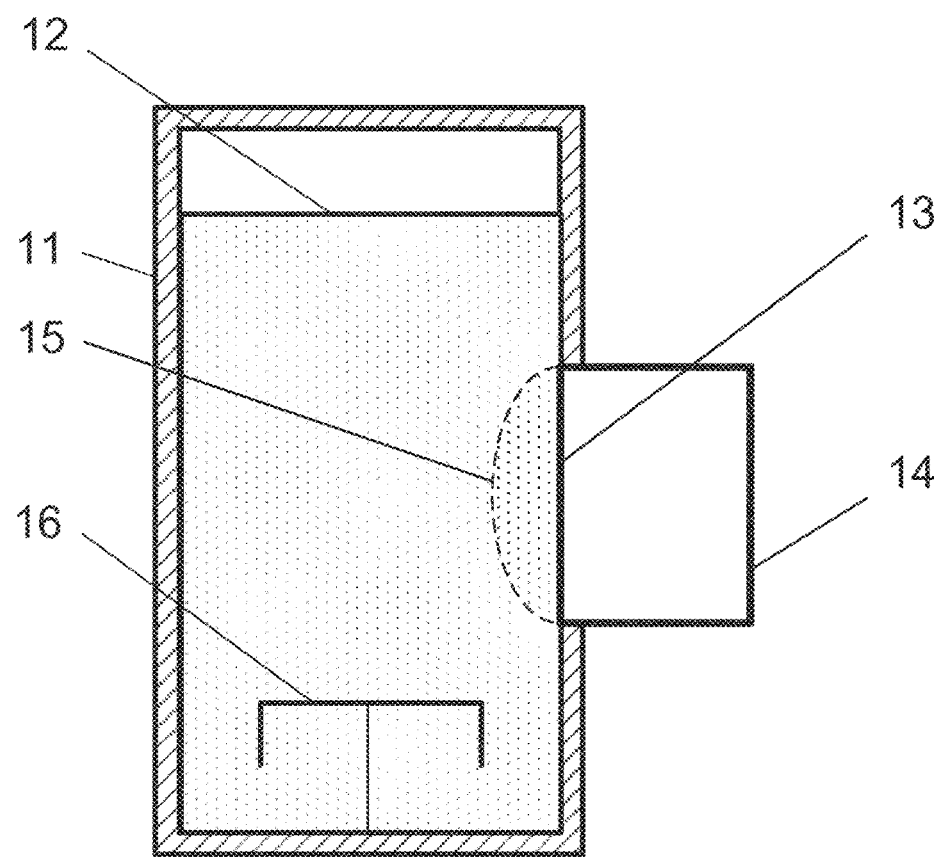
FIG. 1 in schematic form, a sectional view of an apparatus that is suitable for carrying out the method of the present invention.

The invention relates to a method for stimulating the growth of constituents, which are contained in a liquid nutrient medium and which are to be cultivated in a bioreactor, by means of ionizing radiation.

Bioreactors are becoming more important for generating energy, for treating sewage or even for the production of vaccines, to name just a few examples. A bioreactor is to be understood to mean hereinafter a vessel, in which specifically cultivated microorganisms, cells or other constituents are cultivated in a liquid nutrient medium under the most optimum conditions possible, in order to obtain either the microorganisms or cells themselves, parts of them or one of their metabolic products or to break down chemical compounds. The term "biomass" is to be considered to be hereinafter the sum of those microorganisms, cells and/or other constituents that are cultivated in a bioreactor. As already stated, a biomass is usually mixed with a liquid, which also acts as a nutrient medium, inside a bioreactor.

In order to promote the growth of the biomass cultivated in a bioreactor, priority is given to the optimization of the environmental factors inside the bioreactor, such as temperature, pressure, supply air and exhaust air as well as the nutrient conditions for the constituents to be cultivated.

A variety of methods are known for promoting and stimulating the growth of a biomass in a bioreactor. In order to promote the growth of algae or cyanobacteria in a vessel filled with an aqueous solution, it is proposed in the patent document WO 2011/116969 A1 that a side stream of the aqueous solution be removed from the vessel, be saturated with carbon dioxide and be fed back into the vessel in the vicinity of the bottom. The drawback with this method is that this procedure can be used only for a few types of microorganisms.

A hypothesis, according to which harmful or toxic substances, administered in very low doses, may have a positive effect on organisms is known under the term "hormesis". In the case of various substances, such as, for example, digitalis, colchinine or opium, such a positive effect has already been demonstrated. It is also known from laboratory experiments that ionizing radiation, administered in very low doses, has a so-called biopositive effect on viruses, bacteria, fungi and algae [E. Lengfelder, "Is there also a biopositive effect of ionizing radiation?", "Low Dose Radiation and Health", pages 97-102], a process that is also referred to by the term "radiation hormesis". Thus, for example, in the case of algae a growth acceleration after x-irradiation and in the case of bacteria and amoebae an increase in the fission activity after the administration of a low radiation dose could be determined. This radiation hormesis is also mentioned by M. G. Vicker et al. in "Hormesis and the Biological Effect of Ionizing Radiation: Experiments with Lung Fibroblasts", "The Effect of Low Radiation Doses", page 243 et seq., where it is pointed out that ionizing radiation stimulates the DNA repair systems in E. coli. Specific process steps, such as such a radiation treatment with a low radiation dose outside laboratory conditions, can be carried out on a larger biomass, but are not known from the latter two publications.

Therefore, the present invention is based on the technical problem of providing a method for stimulating the growth of a biomass inside a bioreactor, by means of which the disadvantages of the prior art can be overcome. In particular, the method of the present invention is intended to make it possible to stimulate also larger volumes of a biomass in a bioreactor with respect to growth, where in this case, the method is intended to allow a homogeneous treatment of the entire biomass.

In the method according to the invention, the stimulation of the growth of biomass, which is present mixed with a liquid within a bioreactor, takes place through the application of ionizing radiation. The ionizing radiation used here is preferably low-energy electrons generated and accelerated by an electron source and/or X-rays generated by the electron source. Electrons having an acceleration voltage of 25 keV to 300 keV are to be considered to be low-energy electrons in the context of the present invention.

As already stated above, the biomass inside a bioreactor usually is mixed with a liquid. If a liquid or a partial liquid volume inside a bioreactor is specified below, then the specified liquid also comprises the biomass contained in the liquid, or the specified partial liquid volume also comprises the partial amount of the biomass that is mixed in the partial liquid volume.

While prior art methods often attempt to complete the entire treatment of a batch of material with ionizing radiation in one radiation pass, with high-energy, accelerated electrons usually being used when electron beams are employed, the method of the present invention is based on exposing only partial volumes of a batch of material to ionizing radiation for this purpose, however, repeatedly and with very low doses of ionizing radiation.

Therefore, in the method of the present invention, only a first partial volume of a liquid, located in a bioreactor, is exposed to ionizing radiation, the first partial volume comprising at most 10% of the liquid volume in the bioreactor. Then, the first partial volume of the liquid, which has been exposed to ionizing radiation, is mixed with the second partial liquid volume, which has not been exposed to ionizing radiation, in the bioreactor. Then the process steps of irradiating a first partial volume of the liquid, located in the bioreactor, with ionizing radiation and of mixing the first partial volume with the second partial volume are repeated several times. It is known that in order to stimulate the growth of a biomass as a function of the type of constituents of a biomass, different total doses of ionizing radiation may be optimal for a stimulation process. In the method of the present invention, the repetition of the two process steps of exposing a first partial volume to ionizing radiation and of mixing the first partial volume, which has been exposed to ionizing radiation, with the second partial volume is terminated not later than when each partial volume of the liquid in the bioreactor has been exposed to a total radiation dose of 50 Gy on statistical average. However, the total radiation dose can also be selected so as to be less than 50 Gy, depending on the type of constituents of a biomass. Which total radiation dose for a type of constituents of a biomass is optimal to stimulate the growth of the biomass can be determined on the basis of laboratory tests.

Exposing only a relatively small first partial volume of a liquid in a bioreactor to ionizing radiation; irradiating the first partial volume during one radiation pass with a relatively small radiation dose in relation to the total radiation dose; and mixing the liquid in the bioreactor several times, results in the entire liquid in the bioreactor and, thus, also the entire biomass in the bioreactor, being exposed to a homogeneous total dose of ionizing radiation on statistical average, which is a process that correlates with a homogeneous stimulation of the growth of the biomass when viewed over the total volume of the biomass. In so doing, the smaller a first partial volume of the liquid in the bioreactor is selected, the more advantageous the effect of the process is. Therefore, in one embodiment, a first partial volume is selected that comprises at most 5% of the total volume of the liquid in the bioreactor.

It is known that the average depth of penetration of low-energy electrons into a medium and the distribution of the energy introduced into the medium, when said distribution is viewed over the depth of penetration, can be calculated. As a function thereof, it is possible for a person skilled in the art to adjust the electrical parameters of an electron source in such a way that only a maximum of 10%, and preferably a maximum of 5%, of the total volume of a liquid, located in a bioreactor, is exposed to the low-energy electrons generated by the electron source. In accordance with the invention, a partial volume is considered to have been exposed to the low-energy electrons of an electron source when at least 90% of the energy of the low-energy electrons generated by the electron source is introduced into this partial volume.

As already pointed out above, it is also advantageous if, during an irradiation passage of a first partial volume, only a low dose of ionizing radiation is also introduced into the first partial volume. Therefore, in another embodiment, a first partial volume of the liquid in the bioreactor is exposed to only 1% of the total dose of ionizing radiation that is required to stimulate the growth of the partial amount of the biomass, contained in the first partial volume of the liquid, during one radiation pass.

The application of such a low dose of ionizing radiation to a relatively small first partial volume to be irradiated makes it necessary that, in order to stimulate the growth of the entire biomass in the bioreactor, it is necessary for a first partial volume to be irradiated multiple times, and for a currently irradiated first partial volume to be thoroughly mixed multiple times with a respective currently unirradiated second partial volume, an aspect that, however, has the aforementioned advantage that all of the particles in the bioreactor are exposed to an identical total dose of ionizing radiation on statistical average.

Therefore, the method of the present invention is also particularly suitable when larger volumes of a biomass are to be stimulated with respect to growth, such as, for example, in bioreactors having a holding capacity of several hundred or even several thousand liters.

In one embodiment of the method of the present invention, a subarea of a wall of the bioreactor is designed as an electron exit window of the electron source, through which window low-energy electrons penetrate into the first partial volume of the liquid inside the bioreactor, where in this case the means for mixing the liquid in the bioreactor have the effect that the composition of the first partial volume of the liquid in the bioreactor changes.

As an alternative, however, the first partial volume of the liquid volume can also be removed from the bioreactor, can be exposed to low-energy electrons outside the bioreactor and then mixed with the second liquid volume, remaining in the bioreactor.

As already described once above, the growth of a biomass can be stimulated, according to the invention, by introducing the energy of low-energy electrons of an electron source, and/or by introducing x-rays generated by the electron source, into the first partial volume. As is well-known, x-rays are always generated at the same time that accelerated electrons are generated by means of an electron source. The type of material and/or the thickness of the electron exit window, pertaining to an electron source, can be used to adjust the ratio of the low-energy electrons introduced into a medium, and the x-rays introduced into the medium. If the thickness of an electron exit window is increased while the material of the electron exit window remains the same, then the above described ratio is shifted in favor of the x-rays introduced into the medium. Since, on the one hand, there are biomass particles in which the growth preferably is stimulated by the application of low-energy electrons and, on the other hand, there are biomass particles in which the growth stimulated is preferably by the application of x-rays, it is possible to adjust whether more low-energy electrons or more x-rays should be introduced into a biomass by a suitable choice of material for the electron exit window and/or by a suitable choice of the thickness of the electron exit window.

In one embodiment, the stimulation process for the growth of a biomass is carried out only once, after the liquid, mixed with a biomass, has been filled into the associated bioreactor. As an alternative, the stimulation process can also be repeated at intervals of a few minutes up to several months.

The present invention is explained in more detail below with reference to exemplary embodiments.

FIG. 1 shows, in schematic form, a sectional view of an apparatus that is suitable for carrying out the method of the present invention. First, a liquid volume 12 of a liquid, mixed with a biomass, is filled into a bioreactor 11. A wall of the bioreactor 11 is formed in one region as an electron exit window 13 of an electron source 14. In order to stimulate the growth of the biomass, low-energy electrons having an acceleration voltage of 25 keV to 300 keV pass through the electron exit window 13 into a first partial volume 15 of the liquid volume 12. Since, as already mentioned, the penetration depth of accelerated electrons and the distribution of the energy introduced into the liquid at the same time can be calculated, a person skilled in the art can adjust, according to the present invention, the electrical parameters of the electron source 14 in such a way that the first partial volume 15, which has been exposed to the low-energy electrons of the electron source 14, amounts to a maximum of 10%, and preferably at most 5%, of the liquid volume 12 and that at least 90% of the energy of the low-energy electrons is introduced into this first partial volume 15.

Preferably the first partial volume 15 of the liquid is exposed to at most 1% of the total amount of low-energy electrons that is needed to stimulate the biomass particles, which are mixed with the first partial volume 15, during an irradiation time span. In laboratory tests it is possible to determine what dose of low-energy electrons is required to stimulate all of the biomass particles of a partial volume 15. As a function thereof, the electrical parameters of the electron source 14 can also be adjusted by a person skilled in the art in such a way that during an irradiation time span at most 1% of the total amount of low-energy electrons, which are needed to stimulate all of the biomass particles within the partial volume 15, penetrate into the partial volume 15.

Means 16 ensure that a first partial volume 15, which has been exposed to low-energy electrons, is mixed with the second partial volume, which has not been exposed to low-energy electrons, as a result of which the composition of the first partial volume 15 is also changed; and, thus, a new first partial volume 15 is formed continuously.

The exposure of the first partial volume 15 to low-energy electrons and the mixing of the liquid in the bioreactor 11 are continued until all of the biomass particles are exposed to the total dose of low-energy electrons, required to stimulate, on statistical average. In accordance with the invention, each partial volume of the liquid in the bioreactor 11 is exposed to a dose of at most 50 Gy on statistical average.

In one embodiment, the electron source 14 is operated continuously and at constant power during the entire process of stimulating all of the biomass particles in the bioreactor 11. As an alternative, however, the electron source 14 can also be activated only periodically at time intervals, wherein the time segments of activation of the electron source can be pf the same length or of different lengths.

In a further embodiment, the liquid in the bioreactor 11 is mixed continuously with the means 16 during the entire stimulation process of all of the biomass particles within the liquid volume 12 in the bioreactor 11. As an alternative, the liquid in the bioreactor 11 can also be mixed only periodically at time intervals, wherein the time intervals are of the same length or of different lengths.

Figure 2:
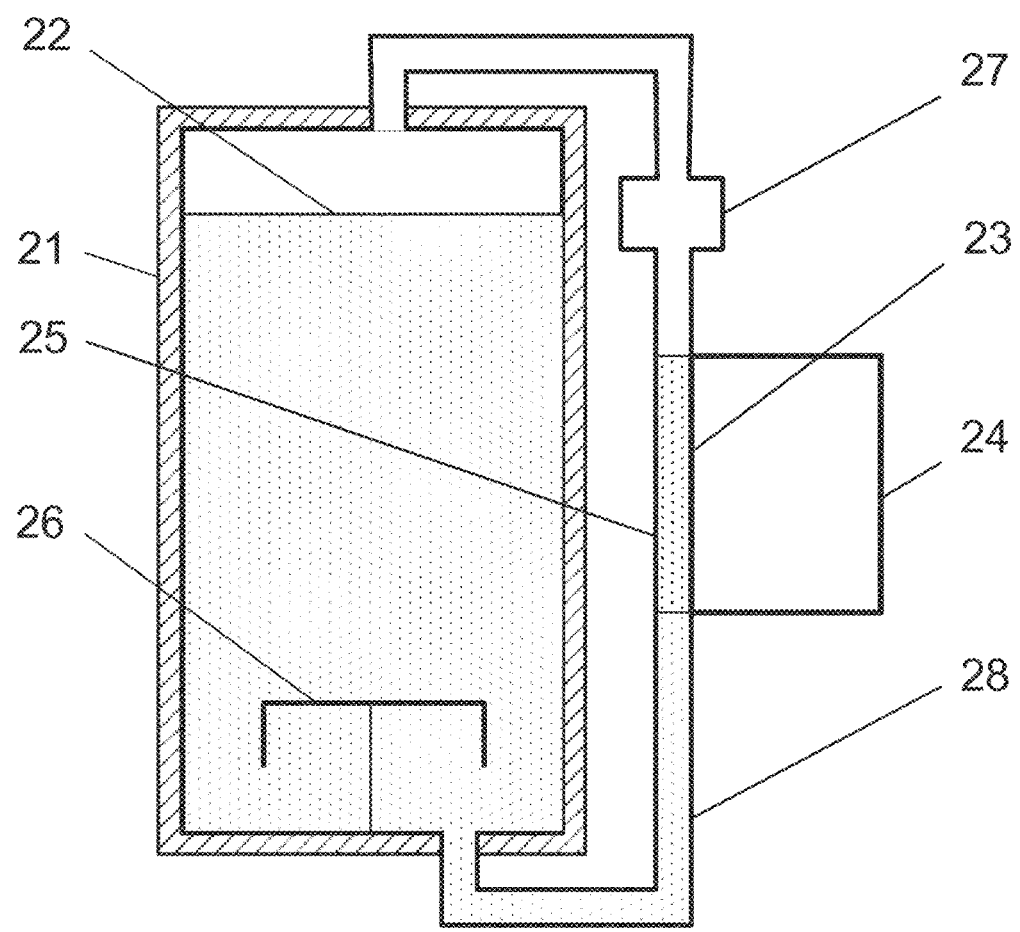
FIG. 2 in schematic form, a sectional view of an alternative apparatus that is suitable for carrying out the method of the present invention.

An alternative apparatus for carrying out the method of the present invention is shown in schematic form as a sectional view in FIG. 2. First, a bioreactor 21 is filled with a liquid volume 22 of a liquid, which is mixed with a biomass and in which the growth of the biomass particles is to be stimulated. A continuous stream of the liquid located in the bioreactor 21 is branched off by means of at least one pump apparatus 27, is conveyed through a pipeline 28, and then fed back again to the bioreactor 21.

A wall of the pipeline 28 is formed in one region as an electron exit window 23 of an electron source 24. Low-energy electrons having an acceleration voltage of 25 keV to 300 keV pass through the electron exit window 23 into a first partial volume 25 of the liquid volume 22. In this case the pipeline 28 and the electron source 24 are dimensioned in such a way that the low-energy electrons, generated by the electron source 24, are applied only to a first partial volume 25, which amounts to a maximum of 10% and preferably at most 5% of the liquid volume 22, with at least 90% of the energy of the low-energy electrons being introduced into the first partial volume 25.

In this procedure, the flow velocity of the liquid in the pipeline 28 and the electrical parameters of the electron source 24 are adjusted in such a way that at most 1% of the total amount of low-energy electrons, which are needed to stimulate all of the biomass particles within the first partial volume 25, penetrate into a first partial volume 25 in one run (that is, when said partial volume flows once past the electron exit window 25).

The exposure of the first partial volume 25 to low-energy electrons and the mixing of the liquid in the bioreactor 21 are continued until a previously calculated total dose of low-energy electrons has been introduced into the liquid volume 22.

If, as shown in FIG. 2, the continuous flow of the liquid, located in the bioreactor 21, is branched off in a lower region of the bioreactor 21 and is fed back again into an upper region of the bioreactor 21, then this process alone ensures that the liquid, located in the bioreactor 21 is mixed continuously. In addition, however, the liquid located in the bioreactor 21 can also be mixed continuously or at time intervals with the aid of means 26.

The inventive procedures, described with reference to FIGS. 1 and 2, ensure the application of a continuously homogeneous dose of accelerated electrons in relation to the entire volume of liquid in a bioreactor and are, thus, suitable for stimulating the growth of a biomass. The method of the present invention can be used, for example, in bioreactors for producing vaccines or even in the treatment of sewage.

In the exemplary embodiments described with reference to FIGS. 1 and 2, at least one sensor can also be arranged within the regions of the first partial volumes 15 or 25, respectively. With said sensor, the intensity of the stream of accelerated, low-energy electrons, their distribution in the partial volume 15 or 25, respectively, and/or the dose of the low-energy electrons applied in the partial volume 15 or 25, respectively, can be detected and controlled by means of an evaluation apparatus.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A method for stimulating growth of a biomass, the method comprising:
   exposing a first partial volume of a liquid located in a bioreactor to an ionizing radiation, the first partial volume comprising at most 10% of the liquid volume in the bioreactor, wherein said liquid comprises a biomass contained in the liquid, the biomass comprising a microorganism, animal cell, and/or plant cell;
   mixing the first partial liquid volume, which has been exposed to the ionizing radiation, with a second partial liquid volume, which has not been exposed to ionizing radiation, in the bioreactor; and
   repeating the exposing of the first partial liquid volume to ionizing radiation and the mixing of the first partial liquid volume with the second partial liquid volume, the total liquid volume of the bioreactor, and/or the total contents therein, being exposed to a total radiation dose of at most 50 Gy on statistical average, sufficient to stimulate growth of the biomass.

2. The method of claim 1, wherein the ionizing radiation comprises a plurality of accelerated, low-energy electrons having an acceleration voltage of 25 keV to 300 keV and/or x-rays.

3. The method of claim 2, further comprising
removing the first partial liquid volume of the liquid from the bioreactor,
exposing the first partial liquid volume to the low-energy electrons and/or x-rays outside the bioreactor, and thereafter
mixing the exposed first partial liquid volume with the second partial liquid volume, remaining in the bioreactor.

4. The method of claim 3, wherein a continuously flowing liquid stream is branched off from the bioreactor, guided past an electron exit window of an electron source outside the bioreactor, and therein:
exposing the continuously flowing liquid stream to the low-energy electrons and/or x-rays, and
feeding the exposed first partial liquid volume back into the bioreactor.

5. The method of claim 3, wherein mixing the exposed first partial liquid volume with the second partial liquid volume comprises mixing the liquid in the bioreactor continuously.

6. The method of claim 2, wherein exposing of the first partial liquid volume to ionizing radiation comprises introducing at least 90% of the energy of the low-energy electrons into the first partial volume.

7. The method of claim 1, wherein a subarea of a wall of the bioreactor is formed as an electron exit window of an electron source, through which low-energy electrons and/or x-rays penetrate into the first partial volume of the liquid inside the bioreactor, wherein the mixing the liquid in the bioreactor has the effect that the composition of the first partial volume of the liquid in the bioreactor changes.

8. The method of claim 7, wherein repeating the exposing of the first partial liquid volume comprises operating the electron source continuously.

9. The method of claim 7, wherein repeating the exposing of the first partial liquid volume comprises activating the electron source periodically.

10. The method of claim 1, wherein mixing the first partial liquid volume with the second partial liquid volume comprises mixing the liquid in the bioreactor continuously.

11. The method of claim 1, wherein mixing the first partial liquid volume with the second partial liquid volume comprises mixing the liquid in the bioreactor periodically.

12. The method of claim 1, wherein the first partial liquid volume comprises at most 5% of the liquid volume in the bioreactor.

* * * * *